United States Patent [19]

Coates et al.

[11] Patent Number: 4,939,144

[45] Date of Patent: Jul. 3, 1990

[54] TRICYCLIC KETONE DERIVATIVES AS 5-HT ANTAGONISTS

[75] Inventors: Ian H. Coates, Hertford; David C. Humber, London; James A. Bell, Royston; George B. Ewan, Gerrards Cross; Alexander W. Oxford, Royston; William L. Mitchell, London, all of England

[73] Assignee: Glaxo Group Limited, London, United Kingdom

[21] Appl. No.: 260,680

[22] Filed: Oct. 21, 1988

[30] Foreign Application Priority Data

Oct. 22, 1987 [GB] United Kingdom ............... 8724729
Feb. 8, 1988 [GB] United Kingdom ............... 8802808

[51] Int. Cl.$^5$ ................... A61K 31/55; C07D 409/08
[52] U.S. Cl. ................................. 514/212; 514/319; 514/323; 514/324; 514/397; 540/603; 546/196; 546/200; 546/202; 548/336
[58] Field of Search ............... 548/336; 514/397, 212, 514/324, 319, 323; 540/603; 546/196, 202, 200

[56] References Cited

U.S. PATENT DOCUMENTS

| | | | |
|---|---|---|---|
| 4,808,581 | 2/1989 | Oxford et al. | 514/212 |
| 4,814,344 | 3/1989 | Humber et al. | 514/397 |
| 4,822,881 | 4/1989 | Coates et al. | 540/603 |
| 4,859,662 | 8/1989 | Coates et al. | 514/212 |

FOREIGN PATENT DOCUMENTS

| | | |
|---|---|---|
| 87/67121 | 7/1987 | Australia . |
| 191562 | 8/1986 | European Pat. Off. . |
| 210840 | 2/1987 | European Pat. Off. . |
| 219193 | 4/1987 | European Pat. Off. . |
| 219929 | 4/1987 | European Pat. Off. . |
| 221629 | 5/1987 | European Pat. Off. . |
| 247266 | 12/1987 | European Pat. Off. . |
| 338650 | 10/1989 | European Pat. Off. . |
| 2153821A | 8/1985 | United Kingdom . |

Primary Examiner—Richard A. Schwartz
Attorney, Agent, or Firm—Bacon & Thomas

[57] ABSTRACT

The invention relates to ketones of the general formula (I):

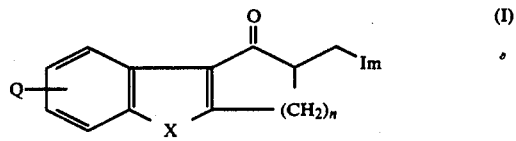

wherein Im represents an imidazolyl group of the formula:

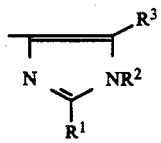

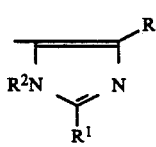

or

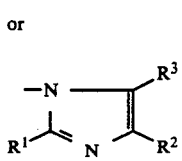

one of the groups represented by $R^1$, $R^2$ and $R^3$ is a hydrogen atom or a $C_{1-6}$alkyl, $C_{3-7}$cycloalkyl, $C_{3-6}$alkenyl, phenyl or phenyl $C_{1-3}$alkyl group, and each of the other two groups, which may be the same or different, represents a hydrogen atom or a $C_{1-6}$alkyl group; n represents 1, 2 or 3;

Q represents a hydrogen atom, a halogen atom, or a hydroxy, $C_{1-4}$alkoxy, phenyl $C_{1-3}$alkoxy or $C_{1-6}$alkyl group, or a group $-NR^4R^5$ or $-CONR^4R^5$, (wherein $R^4$ and $R^5$, which may be the same or different, each represents a hydrogen atom or a $C_{1-4}$alkyl or $C_{3-4}$alkenyl group, or together with the nitrogen atom to which they are attached form a saturated 5 to 7 membered ring);

and X represents an oxygen or a sulphur atom, or, when Im represents an imidazolyl group of formula (c) and n represents 1 or 3, X may also represent the group $NR^6$, wherein $R^6$ represents a hydrogen atom or a group selected from $C_{1-10}$alkyl, $C_{3-6}$alkenyl, $C_{3-10}$alkynyl, $C_{3-7}$cycloalkyl, $C_{3-7}$cycloalkyl $C_{1-4}$alkyl, phenyl, phenyl $C_{1-3}$alkyl, $-CO_2R^7$, $-COR^7$, $-CONR^7R^8$ or $-SO_2R^7$ (wherein $R^7$ and $R^8$, which may be the same or different, each represents a hydrogen atom, a $C_{1-6}$alkyl, or $C_{3-7}$cycloalkyl group, or a phenyl or phenyl $C_{1-4}$alkyl group, in which the phenyl group is optionally substituted by one or more $C_{1-4}$alkyl, $C_{1-4}$alkoxy or hydroxy groups or halogen atoms, with the proviso that $R^7$ does not represent a hydrogen atom when $R^6$ represents a group $-CO_2R^7$); and physiologically acceptable salts and solvates thereof.

The compounds are potent and selective antagonists of the effect of 5-HT and 5-HT$_3$ receptors and are useful, for example, in the treatment of psychotic disorders, anxiety, and nausea and vomiting.

10 Claims, No Drawings

TRICYCLIC KETONE DERIVATIVES AS 5-HT ANTAGONISTS

This invention relates to tricyclic ketones, to processes for their preparation, to pharmaceutical compositions containing them and to their medical use.

In particular the invention relates to compounds which are potent and selective antagonists of 5-hydroxytryptamine (5-HT) at 5-HT receptors of the type located on terminals of primary afferent nerves. Receptors of this type are now designated as 5-HT$_3$ receptors and are also present in the central nervous system. 5-HT occurs widely in the neuronal pathways in the central nervous system and disturbance of these 5-HT containing pathways is known to alter behavioural syndromes such as good, psychomotor activity, appetite and memory.

Compounds having antagonist activity at 5-HT$_3$ receptors have been described previously.

Thus for example published UK Patent Specification No. 2153821A and published European Patent Specifications Nos. 191562, 219193 and 210840 disclose 3-imidazolylmethyltetrahydrocarbazolones which may be represented by the general formula:

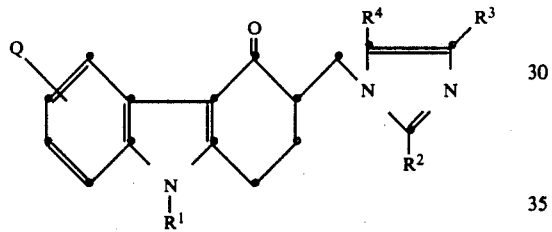

wherein R$^1$ represents a hydrogen atom or a group selected from C$_{1-10}$alkyl, C$_{3-6}$ alkenyl, C$_{3-10}$ alkynyl, C$_{3-7}$cycloalkyl, C$_{3-7}$cycloalkylC$_{1-4}$alkyl, phenyl or phenylC$_{1-3}$alkyl, and in the case where Q represents a hydrogen atom, R$^1$ may also represent —CO$_2$R$^5$, —COR$^5$, —CONR$^5$R$^6$ or —SO$_2$R$^5$ (wherein R$^5$ and R$^6$, which may be the same or different each represents a hydrogen atom, a C$_{1-6}$ alkyl or C$_{3-7}$cycloalkyl group, or a phenyl or phenylC$_{1-4}$alkyl group, in which the phenyl group is optionally substituted by one or more C$_{1-4}$ alkyl, C$_{1-4}$alkoxy or hydroxy groups or halogen atoms, with the priviso that R$^5$ does not represent a hydrogen atom when R$^1$ represents a group —CO$_2$R$^5$ or —SO$_2$R$^5$);

one of the groups represented by R$^2$, R$^3$ and R$^4$ is a hydrogen atom or a C$_{1-6}$ alkyl, C$_{3-7}$ cycloalkyl, C$_{2-6}$ alkenyl, or phenylC$_{1-3}$alkyl group, and each of the other two groups, which may be the same or different, represents a hydrogen atom or a C$_{1-6}$ alkyl group;

Q represents a hydrogen atom or a halogen atom or a hydroxy,

C$_{1-4}$alkoxy, phenylC$_{1-3}$alkoxy or C$_{1-6}$ alkyl group or a group —NR$^7$R$^8$ or —CONR$^7$R$^8$ (wherein R$^7$ and R$^8$, which may be the same or different, each represents a hydrogen atom or a C$_{1-4}$ alkyl or C$_{3-4}$ alkenyl group, or together with the nitrogen atom to which they are attached form a saturated 5 to 7 membered ring); and physiologically acceptable salts and solvates thereof.

We have now found a novel group of compounds which differ in structure from those described previously, and which are potent antagonists of the effect of 5-HT at 5-HT$_3$ receptors.

The present invention provides a tricyclic ketone of the general formual (I):

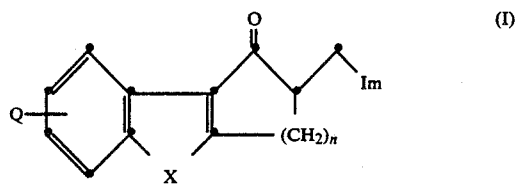

wherein Im represents an imidazolyl group of the formula:

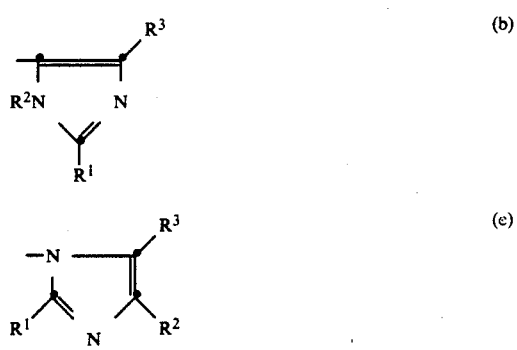

and one of the groups represented by R$^1$, R$^2$ and R$^3$ is a hydrogen atom or a C$_{1-6}$alkyl, C$_{3-7}$cycloalkyl, C$_{3-6}$alkenyl, phenyl or phenylC$_{1-4}$alkyl group, and each of the other two groups, which may be the same or different, represents a hydrogen atom or a C$_{1-6}$ alkyl group;

n represents 1, 2 or 3;

Q represents a hydrogen atom, a halogen atom, or a hydroxy, C$_{1-4}$alkoxy, phenylC$_{1-3}$alkoxy or C$_{1-6}$ alkyl group, or a group —NR$^4$R$_5$ or —CONR$^4$R$^5$ (wherein R$^4$ and R$^5$, which may be the same or different, each represents a hydrogen atom or a C$_{1-4}$ alkyl or C$_{3-4}$ alkenyl group, or together with the nitrogen atom to which they are attached form a saturated 5 to 7 membered ring);

and X represents an oxygen or a sulphur atom, and, when Im represents an imidazolyl group of formula (c) and n represents 1 or 3, X may also represent the group NR$^6$, wherein R$^6$ represents a hydrogen atom or a group selected from C$_{1-10}$alkyl, C$_{3-6}$alkenyl, C$_{3-10}$alkynyl, C$_{3-7}$cycloalkyl, C$_{3-7}$cycloalkylC$_{1-4}$alkyl, phenyl, phenylC$_{1-3}$alkyl, —CO$_2$R$^7$, —COR$^7$, —CONR$^7$R$^8$ or —SO$_2$R$^7$ (wherein R$^7$ and R$^8$, which may be the same or different, each represents a hydrogen atom, a C$_{1-6}$ alkyl or C$_{3-7}$ cycloalkyl group, or a phenyl or phenylC$_{1-4}$alkyl group, in which the phenyl group is optionally substituted by one or more C$_{1-4}$ alkyl, C$_{1-4}$ alkoxy or hydroxy groups or halogen atoms, with the proviso that R$^7$ does not represent a hydrogen atom when $R^6$ represents a group $-CO_2R^7$ or $-SO_2R^7$);

and physiologically acceptable salts and solvates thereof.

According to one aspect, the invention provides compounds of formula (I) wherein X represents an oxygen or a sulphur atom and Im represents an imidazolyl group of formula (a) or (b) ($R^1$, $R^2$, $R^3$, n and Q being as defined in formula (I)).

According to another aspect, the invention provides compounds of formula (I) wherein Im represents an imidazolyl group of formula (c), Q represents a hydrogen atom, X represents an oxygen or a sulphur atom, and, when n represents 1 or 3, X may also represent the group $NR^6$, wherein $R^6$ represents a hydrogen atom or a group selected from $C_{1-10}$ alkyl, $C_{3-6}$ alkenyl, $C_{3-10}$ alkynyl, $C_{3-7}$ cycloalkyl, $C_{3-7}$cycloalkyl$C_{1-4}$alkyl, phenyl or phenyl$C_{1-3}$alkyl ($R^1$, $R^2$, $R^3$ and n being as defined in formula (I)).

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

It will be appreciated that the carbon atom between the carbonyl group and the group $-(CH_2)_n-$ is asymmetric and may exist in the R- or S-configuration. Furthermore, depending on the nature of the substituents $R^1$, $R^2$, $R^3$, Q and X, centres of optical and geometric isomerism may occur elsewhere in the molecule.

All optical isomers of compounds of general formula (I) and their mixtures including the racemic mixtures thereof, and all the geometric isomers of compounds of formula (I), are embraced by the invention.

Referring to the general formula (I), an alkyl group may be a straight chain or branched chain alkyl group, for example, methyl, ethyl, n-propyl, prop-2-yl, n-butyl, but-2-yl, 2-methylprop-2-yl, n-pentyl, pent-3-yl or n-hexyl. A $C_{3-6}$ alkenyl group may be, for example, a propenyl or butenyl group. When $R^6$ represents a $C_{3-6}$alkenyl or $C_{3-10}$alkynyl group, or Im represents an imidazolyl group of formula (a) or (b) and $R^2$ represents a $C_{3-6}$alkenyl group, or $R^4$ or $R^5$ represents a $C_{3-4}$alkenyl group, the double or triple bond may not be adjacent to the nitrogen atom. A phenyl$C_{1-3}$alkyl group may be, for example, a benzyl, phenethyl or 3-phenylpropyl group. A $C_{3-7}$cycloalkyl group may be, for example, a cyclopropyl, cyclobutyl, cyclopentyl, cyclohexyl or cycloheptyl group. A $C_{1-4}$ alkoxy group may be, for example, a methoxy group. A halogen atom may be, for example, a fluorine, chlorine or bromine atom.

The substituent Q may be at any position in the benzenoid ring.

A preferred class of compounds of formula (I) is that in which Im represents an imidazolyl group of formula (a) or (b).

Another preferred class of compounds of formula (I) is that in which $R^1$, $R^2$ and $R^3$ each independently represents a hydrogen atom or a $C_{1-6}$ alkyl group, more particularly a hydrogen atom or a $C_{1-3}$ alkyl (e.g. methyl) group.

A further preferred class of compounds of formula (I) is that in which Im represents an imidazolyl group of formula (a) or (b), and $R^1$ and $R^2$ each represent a hydrogen atom and $R^3$ represents a $C_{1-6}$alkyl (e.g. methyl) group.

Another preferred class of compounds of formula (I) is that in which Im represents an imidazolyl group of formula (c), and $R^1$ represents a $C_{1-3}$alkyl (e.g. methyl) group, and $R^2$ and $R^3$ each represent a hydrogen atom.

Another preferred class of compounds of formula (I) is that in which n represents 2.

A further preferred class of compounds of formula (I) is that in which Q represents a hydrogen atom.

A further preferred class of compounds of formula (I) is that in which X represents an oxygen or a sulphur atom or a group $NR^6$ wherein $R^6$ represents a $C_{1-3}$alkyl (e.g. methyl) group.

A preferred group of compounds of formula (I) is that in which $R^1$, $R^2$ and $R^3$ each represent a hydrogen atom or a $C_{1-3}$ alkyl (e.g. methyl) group, X represents an oxygen or sulphur atom or the group $NR^6$ where $R^6$ represents a $C_{1-3}$ alkyl (e.g. methyl) group, and Q represents a hydrogen atom (n and Im being as defined in formula (I)).

Within the above preferred group of compounds, a particularly preferred group of compounds are those in which n represents 2, and Im represents an imidazolyl group of formula (a) or (b); or X represents the group $NR^6$ wherein $R^6$ represents a $C_{1-3}$ alkyl (e.g. methyl) group, n represents 3, and Im represents an imidazolyl group of formula (c).

Preferred compounds of the invention are 3,4-dihydro-2-[(5-methyl-1H-imidazol-4-yl)methyl]-1(2H)-dibenzofuranone, 3,4-dihydro-2-[(5-methyl-1H-imidazol-4-yl)methyl]-1(2H)-dibenzothiophenone and 6,7,8,9-tetrahydro-5-methyl-9-[(2-methyl-1H-imidazol-1-yl)methyl]cyclohept[b]indol-10(5H)-one, and their physiologically acceptable salts and solvates.

The potent and selective antagonism of 5-HT at 5-HT$_3$ receptors by compounds of the invention has been demonstrated by their ability to inhibit 3-(5-methyl-1H-imidazol-4-yl)-1-[1-(methyl-t$_3$)-1H-indol-3-yl]-1-propanone binding in rat entorhinal cortex homogenates (following the general procedure described by G. Kilpatrick et al. in Nature, 1987, 330, 746), and/or by their ability to inhibit the 5-HT-induced depolarisation of the rat isolated vagus nerve preparation.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; pain; dependency on drugs and substances of abuse; depression; or dementia or another cognitive disorder, which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations ay also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine H$_2$-receptor antagonists (e.g. ranitidine, sufotidine, 1-methyl-5-[[3-[3-(1-piperidinylmethyl)phenoxy]propyl]amino]-1H-1,2,4-triazole-3-methanol, cimetidine, famotidine, nizatidine or roxatidine) or H+K+ATPase inhibitors (e.g. omeprazole).

A proposed dose of the compounds off the invention for administration to man (of approximately 70 kg body weight) is 0.001 to 100 mg, preferably 0.01 to 50 mg, more preferably 0.1 to 20 mg of the active ingredient per unit dose expressed as the weight of free base, which could be administered, for example, 1 to 4 times per day. It will be appreciated that it may be necessary to make routine variations to the dosage, depending on the age and condition of the patient. The dosage will also depend on the route of administration.

Compounds of general formula (I) and physiologically acceptable salts or solvates thereof may be prepared by the general methods outlined hereinafter. In the following description, the groups $R^1$, $R^2$, $R^3$, $R^6$, n, and Q are as defined for compouns of general formula (I) unless otherwise stated.

According to a first general process (A), a compound of general formula (I) wherein Im represents an imidazolyl group of formula (a) or (b), may be prepared by hydrogenating a compound of formula (II):

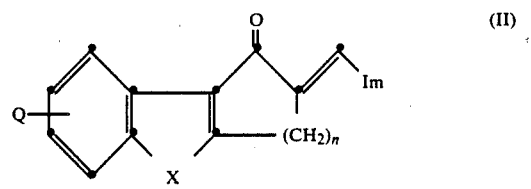

(wherein X represents an oxygen or a sulphur atom and Im represents an imidazolyl group of formula (a) or (b)), or a protected derivative thereof, followed where necessary by removal of any protecting groups.

Hydrogenation according to general process (A) may be effected using conventional procedures, for example using hydrogen in the presence of a noble metal catalyst (e.g. palladium, Raney nickel, platinum or rhodium). The catalyst may be supported on, for example, charcoal or alumina, or alternatively a homogeneous catalyst such as tris(triphenylphosphine)rhodium chloride may be used. The hydrogenation will generally be effected in a solvent such as an alcohol (e.g. methanol or ethanol), an ether (e.g. dioxan), or an ester (e.g. ethyl acetate), or in a mixture of an alcohol and either a hydrocarbon (e.g. toluene) or a halogenated hydrocarbon (e.g. dichloromethane), at a temperature in the range $-20°$ to $+100°$ C., and at a pressure of from 1 to 10 atmospheres.

Compounds of formula (II) are novel compounds and constitute a further aspect of the invention. In addition, they are antagonists of 5-HT at 5-HT$_3$ receptors. Particular compounds of formula (II) are (E)-3,4-dihydro-2-[(5-methyl-1H-imidazol-4-yl)methylene]-1(2H)-dibenzofuranone and (E)-3,4-dihydro-2-[(5-methyl-1H-imidazol-4-yl)methylene]-1(2H)-dibenzothiophenone.

According to another general process (B), a compound of general formula (I) wherein Im represents an imidazolyl group of formula (c), may be prepared by reacting a compound of formula (III):

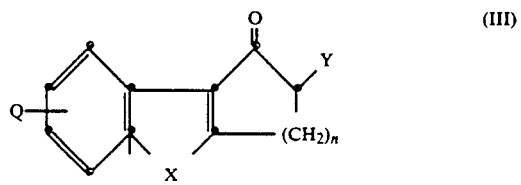

(III)

(wherein X represents an oxygen or sulphur atom or the group NR$^6$, and Y represents a reactive substituent) or a salt or protected derivative thereof, with an imidazole of formula (IV):

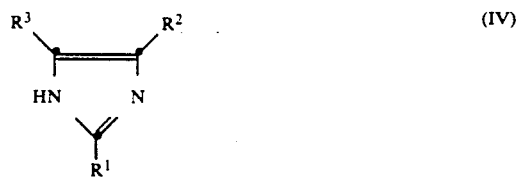

(IV)

or a salt thereof, followed where necessary by deprotection.

Examples of compounds of formula (III) employed as starting materials in the process (B) include compounds wherein Y represents a group selected from an alkenyl group =CH$_2$, or a group of formula —CH$_2$Z where Z represents a readily displaceable atom or group such as a halogen atom (e.g. chlorine, bromine or iodine) an acyloxy group (e.g. trifluoroacetyloxy or acetoxy) or a sulphonyloxy group (e.g. trifluoromethanesulphonyloxy, p-toluenesulphonyloxy or methanesulphonyloxy); a group —N$^+$R$^9$R$^{10}$R$^{11}$L$^-$, where R$^9$, R$^{10}$ and R$^{11}$, which may be the same or different, represent lower alkyl (e.g. methyl), aryl (e.g. phenyl) or aralkyl (e.g. benzyl), or R$^9$ and R$^{10}$ together with the nitrogen atom to which they are attached may form a 5- to 6-membered ring (e.g. a pyrrolidine ring) and L$^-$ represents an anion such as a halide ion (e.g. chloride, bromide or iodide); or a group —NR$^9$R$^{10}$ where R$^9$ and R$^{10}$ are as defined above, for example —N(CH$_3$)$_2$.

When Y represents the group =CH$_2$, the process may conveniently be carried out in a suitable solvent, examples of which include water, esters (e.g. ethyl acetate), ketones (e.g. acetone or methylisobutylketone), amides (e.g. dimethylformamide), alcohols (e.g. ethanol) and ethers (e.g. dioxan or tetrahydrofuran) or mixtures thereof. The process may be effected at a temperature of, for example, 20° to 100° C.

When Y represents the group CH$_2$Z, wherein Z is a halogen atom or an acyloxy or sulphonyloxy group, the process may conveniently be carried out in a suitable solvent such as an amide (e.g. dimethylformamide), an alcohol (e.g. methanol or industrial methylated spirit), or a haloalkene (e.g. dichloromethane), at a temperature of from $-10°$ to $+150°$ C., e.g. $+20°$ to $+100°$ C.

The reaction including a compound of formula (III) where Y represents the group —CH$_2$Z where Z is the group —N$^+$R$^9$R$^{10}$R$^{11}$L$^-$ may conveniently be carried out in a suitable solvent, such as water, an amide (e.g. dimethylformamide), a ketone (e.g. acetone) or an ether (e.g. dioxan) at a temperature of from 20° to 150° C.

The reaction including a compound of formula (III) where Y represents the group —CH$_2$Z, where Z is the group —NR$^9$R$^{10}$, may conveniently be carried out in a suitable solvent such as water or an alcohol (e.g. methanol), or mixtures thereof, or an amide (e.g. dimethylformamide), at a temperature of from 20° to 150° C.

According to another general process (C), a compound of general formula (I) may be converted into another compound of formula (I) using conventional techniques. Such conventional techniques include hydrogenation, alkylation, acylation and acid-catalysed cleavage using protection and deprotection where necessary.

Thus, according to one embodiment of the interconversion process (C), hydrogenation may be used to convert an alkenyl or an alkynyl substituent into an alkyl substituent, or an alkynyl into an alkenyl substituent, or a benzyloxy substituent into a hydroxyl group. Hydrogenation according to general process (C) may be effected using conventional procedures, for example as described above for general process (A).

The term 'alklation' according to general process (C) includes the introduction of other groups such as cycloalkyl, alkenyl or phenalkyl groups.

Thus, for example, a compound of formula (I) n which X represents the group NR$^6$ and R$^6$ represents a C$_{1-10}$alkyl, C$_{3-7}$cycloalkyl, C$_{3-6}$alkenyl, C$_{3-10}$alkynyl, C$_{3-7}$cycloalkylC$_{1-4}$alkyl or phenylC$_{1-3}$alkyl group may be prepared by alkylating the corresponding compound of formula (I) in which R$^6$ represents a hydrogen atom, or a compound of formula (I) in which Im represents an imidazolyl group of formula (a) or (b) and R$^2$ represents a C$_{1-6}$alkyl, C$_{3-7}$cycloalkyl, C$_{3-6}$alkenyl or phenylC$_{1-3}$alkyl group may be prepared by prepared by alkylating the corresponding compound of formula (I) in which R$^2$ represents a hydrogen atom, or a compound of formula (I) in which Q represents a C$_{1-4}$alkoxy group may be prepared by alkylating the corresponding compound in which Q represents a hydroxyl group.

The above alkylation reactions may be effected using conventional procedures, for example as described in published European Patent specification No. 242973.

Thus the reactions may be effected using an appropriate alkylating agent of formula $R^{12}G$ (where $R^{12}$ is the group to be introduced and G is a leaving atom or group), preferably in the presence of a base.

According to another embodiment of general process (C), a compound of formula (I) wherein X represents the group $nR^6$ and $R^6$ represents $-CO_2R^7$, $-COR^7$, $-CON^7R^8$ or $-SO_2R^7$ may be prepared by acylating or sulphonylating as appropriate, a compound of formula (I) wherein $R^6$ represents a hydrogen atom. The acylation/sulphonylation reactions may be effected using an appropriate acylating/sulphonylating agent according to conventional procedures, for example, as described in published European Patent Specification No. 210840.

According to a yet further embodiment of general process (C), a compound of formula (I) in which Q represents a hydroxyl group may be prepared from the corresponding compound of formula (I) in which Q represents a $C_{1-4}$alkoxy or benzyloxy group, by acid-catalysed cleavage. The reaction may be effected using a Lewis acid such as boron tribromide or aluminum trichloride, in a solvent such as a halogenated hydrocarbon (e.g. dichloromethane). The reaction temperature may conveniently be in the range $-80°$ to $+100°$ C.

It should be appreciated that in the above transformations it may be necessary or desirable to protect any sensitive groups in the molecule of the compound in question to avoid undesirable side reactions. For example, it may be necessary to protect the keto group, for example, as a ketal or a thioketal. It may also be necessary to protect the indole or imidazole nitrogen atoms, for example with an arylmethyl (e.g. trityl), arylmethoxymethyl (e.g. phenylmethoxymethyl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group. When Q represents a hydroxyl group it may be necessary to protect the hydroxyl group, for example with an arylmethyl (e.g. benzyl or trityl) group.

Thus according to another general process (D), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons, 1981).

For example a ketal such as an alkyleneketal group may be removed by treatment with a mineral acid such as hydrochloric acid. A thioketal group may be cleaved by treatment with a mercuric salt, (e.g. mercuric chloride), in a suitable solvent, such as ethanol. An arylmethoxymethyl N-protecting group may be cleaved by hydrogenolysis in the presence of a catalyst (e.g. palladium on charcoal). A trityl group may be cleaved by acid hydrolysis (e.g. using dilute hydrochloric or acetic acid). An alkoxyalkyl group may be removed using a mineral acid (e.g. dilute hydrochloric acid). An acyl group may be removed by hydrolysis under acidic or basic conditions (e.g. using hydrogen bromide or sodium hydroxide). A sulphonyl group may be removed by alkaline hydrolysis. An arylmethyl OH-protecting group may be cleaved under acidic conditions (e.g. with dilute acetic acid, hydrobromic acid or boron tribromide) or by hydrogenolysis in the presence of a catalyst (e.g. palladium on charcoal).

Compounds of formula (II) may be prepared by condensing a compound of formula (V):

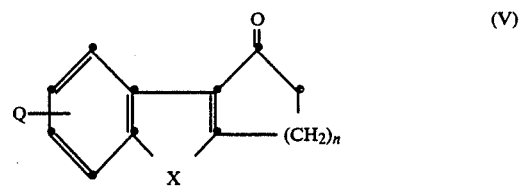

(wherein X represents an oxygen or a sulphur atom), or a protected derivative thereof, with a compound of formula (VI):

$$OHC-Im \quad (VI)$$

(wherein Im represents an imidazolyl group of formula (a) or (b)), or a protected derivative thereof, in the presence of a base such as an alkali metal amide (e.g. lithium diisopropylamide) in an inert solvent such as an ether (e.g. tetrahydrofuran), followed by dehydration of the intermediate carbinol, and removal of any protecting groups where necessary.

The dehydration process may be effected using conventional methods, for example by using an organic or mineral acid (e.g. p-toluenesulphonic, methanesulphonic, trifluoroacetic or hydrochloric acid) in a suitable solvent such as an ether (e.g. tetrahydrofuran), an alcohol (e.g. methanol), or glacial acetic acid, at a temperature in the range of 0° to 100° C.

Compounds of formula (III) may in general be prepared by methods analogous to those described in published U.K. Patent Specification No. 2153821A.

Thus for example, a quaternary salt of formula (II) in which Y represents the group $-CH_2N^+R^9R^{10}R^{11}L^-$ may be prepared from the corresponding tertiary amine of formula (III) in which Y represents the group $-CH_2NR^9R^{10}$ by reaction with an alkylating agent such as methyl iodide or dimethyl sulphate, if preferred in a suitable solvent (e.g. methanol) or an amide (e.g. dimethylformamide). The tertiary amine may be prepared by reaction of a ketone of formula (V) (wherein X represents an oxygen or a sulphur atom or the group $NR^6$) with formaldehyde and the corresponding secondary amine, with heating, for example, at a temperature up to the reflux temperature of the solvent, if desired in a suitable solvent such as an alcohol (e.g. ethanol) or glacial acetic acid.

Compounds of formula (V) in which X represents $NR^6$ are either known compounds or may be prepared by the method described by Y. Oikawa and O. Yonemitsu in J. Org. Chem., 1977, 42, (7), 1213.

Compounds of formula (V) in which X represents an oxygen or a sulphur atom are either known compounds or may be prepared by the methods, or methods analogous to, those described by R. N. Castle et al., J. Heterocycl. Chem., 1985, 22, 215.

Compounds of formula (IV) are either known, or may be prepared by conventional methods.

Compounds of formula (VI) and protected derivatives thereof, are either known, or may be prepared, for example, by the methods described in German Offenlegungsschrift No. 3740352.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), a halogenated hydrocarbon (e.g. dichloromethane), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g a racemic mixture) using conventional means, such as an optically active resolving acid; see for example 'Stereochemistry of Carbon Compounds' by E. L. Eliel (McGraw Hill, 1962) and 'Tables of Resolving Agents' by S. H. Wilen.

The methods described above for preparing the compounds of the invention may be used for the introduction of the desired groups at any stage in the stepwise formation of the required compounds, and it will be appreciated that these methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples. All temperatures are in °C. Thin layer chromatography (t.l.c.) was carried out on silica, and flash column chromatography (FCC) and short-path column chromatography (SPCC) on silica (Merck 9385 and 7747 respectively). Solvent System A as used for chromatography denotes dichloromethane:ethanol:0.88 ammonia solution. Organic extracts were dried, where indicated, over magnesium sulphate or sodium sulphate. The following abbreviations are used: DMF—dimethylformamide; TH—tetrahydrofuran.

INTERMEDIATE 1

2-[(Dimethylamino)methyl]-3,4-dihydro-1(2H)-dibenzofuranone hydrochloride

A mixture of 3,4-dihydro-1(2H)-dibenzofuranone (8.14 g), paraformaldehyde (3.48 g) and dimethylamine hydrochloride (8.55 g) in glacial acetic acid (100 ml) was stirred at 75° under nitrogen for 18 h. The cooled reaction mixture was evaporated, treated with aqueous 2M hydrochloric acid (100 ml), and extracted with ethyl acetate (2×120 ml; discarded). The aqueous phase was brought to pH 9 by the addition of aqueous saturated sodium bicarbonate and then extracted with ethyl acetate (6×150 ml). The combined, dried organic extracts were evaporated to give an oil (9.75 g), a portion (3.00 g) of which was purified by SPCC, eluting with ethylacetate:triethylamine (49:1) to give the free base of the title compound (1.75 g) as an oil. A portion of this oil (1.66 g) was dissolved in ethyl acetate (5 ml) and ether (10 ml), treated with ethereal hydrogen chloride (10 ml), and diluted with ether (60 ml) to precipitate the title compound (1.78 g), m.p. 201°-202°.

INTERMEDIATE 2

9-[(Dimethylamino)methyl]-6,7,8,9-tetrahydro-5-methylcyclohept[b]-indol-10(5H)-one hydrochloride A mixture of 5-methyl-6,7,8,9-tetrahydrocyclohept[-b]indol-10(5H)-one (1.92 g), paraformaldehyde (1.49 g) and dimethylamine hydrochloride (2.2 g) was heated at reflux in a mixture of absolute ethanol (24 ml) and concentrated hydrochloric acid (1 drop) for 21 h. The mixture was added to 8% aqueous sodium bicarbonate (200 ml) and extracted with dichloromethane (2×120 ml). The combined, dried organic extracts were evaporated to give an oil (ca. 3 g) which was dissolved in dry ether (250 ml) and treated with an excess of ethereal hydrogen chloride. The resultant fine suspension was stirred for 1 h and filtered. The collected solid was dried in vacuo to give the title compound (2.6 g), m.p. 185°-188° (decomp.).

INTERMEDIATE 3

2-[(Dimethylamino)methyl]-3,4-dihydro-4-methylcyclopent[b]indol-1(2H)-one

Butyllithium (1.6M in hexane; 3.4 ml) was added dropwise, under nitrogen, at 0° to a stirred solution of diisopropylamine (0.76 ml) in THF (15 ml) and the resulting solution was stirred at 0° for 10 min. before cooling to −78°. A solution of 4-methyl-3,4-dihydrocyclopent[b]indol-1(2H)-one (1 g) in THF (120 ml) was added dropwise at −78° to −70° and the resulting solution was stirred at ca. −78° for 10 min. before N,N-dimethylmethyleneammonium iodide (ca. 1 g) was added. The resulting mixture was allowed to warm to room temperature over 1.5 h and was then partitioned between 2N sodium carbonate (100 ml) and ethyl acetate (2×100 ml). The combined, dried organic extracts were evaporated in vacuo to give an oil which was purified by FCC eluting with System A (100:8:1) to give the title compound (0.14 g) as an oil, t.l.c. (System A 100:8:1) Rf 0.2.

INTERMEDIATE 4

(E)-3,4-Dihydro-2-[(5-methyl-1H-imidazol-4-yl)methylene]-1(2H)-dibenzofuranone

Lithium diisopropylamide mono(tetrahydrofuran) (1.5M in cyclohexane; 3.2 ml) was added dropwise to a solution of 3,4-dihydro-1(2H)-dibenzofuranone (750 mg) in dry THF (15 ml) at −60°. The resultant solution was stirred at −65° for 1 h and 5-methyl-1-(triphenylmethyl)-1H-imidazole-4-carboxaldehyde (1.55 g) was then added. The reaction mixture was stirred for a further 1.5 h, whilst it was allowed to warm to 0°, and was then poured into 8% aqueous sodium bicarbonate (60 ml). The mixture was extracted with dichloromethane (3×25 ml) and the combined organic extracts were dried and evaporated to give a foam (2.3 g) which was purified by FCC eluting with System A (980:20:2) to give a foam (1.67 g). A solution of this foam in a mixture of THF (50 ml) and acetic acid (8 ml) was treated with p-toluenesulphonic acid monohydrate (5.7 g) and the mixture was heated at reflux for 20 h under nitrogen. The resulting solution was added cautiously to 8% aqueous sodium bicarbonate (200 ml) and extracted with dichloromethane (3×80 ml). The combined organic extracts were dried and evaporated to give an oil which was purified by FCC eluting with System A (100:5:0.5) to give the title compound (462 mg) as a solid, t.l.c. (System A 100:3:0.3) Rf 0.1.

INTERMEDIATE 5

(E)-3,4-Dihydro-2-[(5-methyl-1H-imidazol-4-yl)methylene]-1(2H)-dibenzothiophenone Lithium diisopropylamide mono(tetrahydrofuran) (1.5M in cyclohexane; 3.6 ml) was added dropwise to a solution of 3,4-dihydro-1(2H)-dibenzothiophenone (1.0 g) in dry THF (30 ml) at −65°. The resultant solution was stirred at −65° for 1 h and 5-methyl-1-(triphenylmethyl)-1H-imidazole-4-carboxaldehyde (1.9 g) was then added. The reaction mixture was stirred for a further 1.5 h, whilst it was allowed to warm to 0°. The solution was quenched with acetic acid (6 ml) and the resultant suspension was treated with water (10 ml) and p-toluenesulphonic acid (10.2 g). The reaction mixture was heated at reflux for 17 h, added cautiously to 8% aqueous sodium bicarbonate (300 ml), and extracted with dichloromethane (2×120 ml). The combined organic extracts were dried and evaporated to give an oil which was heated at reflux in a mixture of trifluoroacetic acid (60 ml) and concentrated sulphuric acid (0.3 ml) for 40 min. The reaction mixture was concentrated in vacuo to ca. 10 ml, added cautiously to 8% aqueous sodium bicarbonate (300 ml) and the resultant suspension was extracted with dichloromethane (2×120 ml). The combined organic extracts were dried and evaporated to give a foam which was purified by FCC eluting with System A (100:5:0.5) to give the title compound (648 mg) as a solid, m.p. 220°–223°.

EXAMPLE 1

3,4-Dihydro-2-[(2-methyl-1H-imidazol-1-yl)methyl]-1(2H)-dibenzofuranone hydrochloride A stirred mixture of 2-[(dimethylamino)methyl]-3,4-dihydro-1(2H)-dibenzofuranone hydrochloride (1.00 g), 2-methylimidazole (1.47 g) and water (25 ml) was heated under reflux for 20 h. The cooled mixture was acidified to pH 1 with aqueous 2M hydrochloric acid and extracted with ethyl acetate (2×50 ml; discarded). The aqueous layer was basified to pH 8 with aqueous saturated sodium bicarbonate, extracted with ethyl acetate (5×40 ml), and the combined organic extracts were washed with water (50 ml). The organic layer was dried and evaporated, and the residue was crystallised from ethyl acetate to give the free base of the title compound (176 mg). Evaporation of the mother liquors afforded a further quantity of the free base of the title compound (370 mg). A portion of this solid (166 mg) was treated with ethyl acetate (40 ml), filtered, and concentrated to ca. 10 ml. The solution was acidified to pH 1 by the addition of ethanolic hydrogen chloride, and the precipitate was collected to give the title compound (171 mg), m.p. 217°–222°.

Analysis Found: C, 64.55; H, 5.55; N, 8.65; Cl, 11.7; $C_{17}H_{16}N_2O_2.HCl$ requires C, 64.45; H, 5.4; N, 8.85; Cl, 11.2%.

EXAMPLE 2

3,4-Dihydro-2-[(2-methyl-1H-imidazol-1-yl)methyl]-1(2H-dbenzothiophenone hydrochloride 2-[(Dimethylamino)methyl]-3,4-dihydro-1(2H)-dibenzothiophenone hydrochloride (582 mg) was treated with 8% aqueous sodium bicarbonate (80 ml) and extracted with dichloromethane (3×30 ml). The combined, dried organic extracts were evaporated to give an oil. A solution of this oil in dry DMF (15 ml) was treated with iodomethane (0.13 ml) and allowed to stand at room temperature for 4 h. The solution was treated with 2-methylimidazole (493 mg) and heated at 90° for 18 h. The mixture was diluted with 8% aqueous sodium bicarbonate (70 ml) and extracted with dichloromethane (2×30 ml). The combined, dried organic extracts were evaporated to give an oil, which was purified by FCC eluting with System A (200:10:1) to give an oil. A solution of this oil in dry dichloromethane (30 ml) was treated with a slight excess of ethereal hydrogen chloride, and the solution was evaporated to give the title compound (338 mg) as a solid, m.p. 208°–211°.

Analysis Found: C, 60.1; H, 5.0; N, 8.2; Cl, 10.8; $C_{16}H_{16}N_2O_6$. HCl requires C, 59.9; H, 5.0; N, 8.2; Cl, 11.1%.

EXAMPLE 3

6,7,8,9-Tetrahydro-5-methyl-9-[(2-methyl-1H-imidazol-1-yl)methyl]cyclohept[b]indol-10(5H)-one d,l-tartrate A solution of 9-[(dimethylamino)methyl]-6,7,8,9-tetrahydro-5-methylcyclohept[b]indol-10(5H)-one hydrochloride (1.2 g) and 2-methylimidazole (0.39 g) in dry DMF (15 ml) was heated at 100° under nitrogen for 18 h. The mixture was cooled (20°) and evaporated in vacuo to leave a gum which was partitioned between dichloromethane (2×30 ml) and saturated potassium carbonate solution (30 ml). The combined organic extracts were washed with brine (2×30 ml), dried and evaporated to leave a gum (ca. 1.5 g) which was purified by FCC eluting with System A (200:8:1) to give a solid (0.8 g). This was treated with maleic acid (31 mg) in ethanol (15 ml) and the resulting solution was concentrated to ca. 5 ml and diluted with ether (10 ml) to give a gum which was basified by SPCC eluting with System A (200:8:1) to give a solid (0.78 g). The solid was dissolved in a mixture of methanol:ethyl acetate (1:10; 30 ml) and treated with a solution of d,l-tartaric acid (0.39 g) in a mixture of ethyl acetate:methanol (1:1; 5 ml). The resulting solution was concentrated to ca. 15 ml on a steam bath and cooled to precipitate the title compound (0.96 g) as a solid, m.p. 164°–165°.

Analysis Found: C, 60.6; H, 6.0; N, 9.2; $C_{19}H_{21}N_3O$. $C_4H_6O_6$ requires C, 60.3; H, 6.2; N, 9.2%.

EXAMPLE 4

3,4-Dihydro-4-methyl-2-[(2-methyl-1H-imidazol-1-yl)methyl]cyclopent[b]indol-1(2H)-one hydrochloride Iodomethane (0.04 ml) was added to a stirred solution of 3,4-dihydro-4-methyl-2-[(dimethylamino)methyl]cyclopent[b]indol-1(2H)-one (0.14 g) in dry DMF (15 ml) and the resulting solution was stirred at room temperature for 10 min. 2-Methylimidazole (0.14 g) was added and the solution was stirred at 100° for 18 h. A further portion of 2-methylimidazole (0.4 g) was added and the solution was heated at 100° for 3 days. The solution was cooled, partitioned between 2N sodium carbonate (75 ml) and ethyl acetate (2×75 ml) and the combined organic extracts were washed with 2N sodium carbonate (75 ml; discarded), dried and evaporated in vacuo to give an oil. This was purified by FCC eluting with System A (100:8:1) to give the free base of the title compound as an oil. This was dissolved in absolute ethanol (5 ml), acidified with ethereal hydrogen chloride, and the salt was precipitated by adding excess dry ether. The salt was filtered off and dried in vacuo to give the title compound (0.15 g), m.p. 96° (decomp.), t.l.c. (System A 100:8:1) Rf 0.45.

EXAMPLE 5

3,4-Dihydro-2-[(5-methyl-1H-imidazol-4-yl)methyl]-1(2H)-dibenzofuranone maleate

A suspension of (E)-3,4-dihydro-2-[(5-methyl-1H-imidazol-4-yl)methylene]-1(2H)-dibenzofuranone (404 mg) in absolute ethanol (25 ml) was hydrogenated at atmospheric pressure and room temperature for 1 h using a stirred suspension of 10% palladium on charcoal catalyst (40 mg). The suspension was then filtered, the filtrate was treated with maleic acid (168 mg) and the resultant solution was evaporated to give a solid. This solid was heated at reflux in ethyl acetate (50 ml) for 15 min and the resultant suspension was allowed to cool to room temperature. The ethyl acetate was decanted and the remaining solid was dried in vacuo to give the title compound (433 mg), m.p. 168°–170°.

Analysis Found: C, 63.5; H, 5.2; N, 7.0; $C_{17}H_{16}N_2O_2.C_4H_4O_4$ requires C, 63.6; H, 5.1; N, 7.1%.

EXAMPLE 6

3,4-Dihydro-2-[(5-methyl-1H-imidazol-4-yl)methyl]-1(2H)-dibenzothiophenone hydrochloride A mixture of (E)-3,4-dihydro-2-[(5-methyl-1H-imidazol-4-yl) methylene]-1(2H)-dibenzothiophenone (599 mg), 2N hydrochloric acid (2 ml) and ethanol (50 ml) was hydrogenated at atmospheric pressure and room temperature using a 10% palladium on charcoal catalyst (60 mg) for 20 h. The suspension was warmed on a steam bath for 10 min and then filtered. The filtrate was evaporated to give an oil which was purified by FCC eluting with System A (100:10:1) to give a solid. A solution of this solid in a mixture of dichloromethane (20 ml) and methanol (5 ml) was treated with a slight excess of ethereal hydrogen chloride. The solution was evaporated to give the title compound (449 mg), m.p. 266°–269°, t.l.c. (System A 100:10:1) Rf 0.3.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Tablets of other strengths may be prepared by altering the ratio of active ingredient to excipients or the compression weight and using punches to suit.

| Direct Compression Tablet | | |
|---|---|---|
| | mg/tablet | |
| Active Ingredient | 0.50 | 10.00 |
| Calcium Hydrogen Phosphate BP* | 87.25 | 77.75 |
| Croscarmellose Sodium NF | 1.80 | 1.80 |
| Magnesium Stearate BP | 0.45 | 0.45 |
| Compression weight | 90.00 | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

| INJECTION FOR INTRAVENOUS ADMINISTRATION | | |
|---|---|---|
| | mg/ml | |
| Active Ingredient | 0.05 | 1.0 |
| Sodium Chloride BP | as required | as required |

| INJECTION FOR INTRAVENOUS ADMINISTRATION -continued | | |
|---|---|---|
| | mg/ml | |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

We claim:

1. A compound of formula (I):

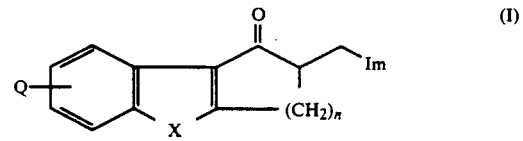

wherein Im represents an imidazolyl group of the formula:

or

one of the groups represented by $R^1$, $R^2$ and $R^3$ is a hydrogen atom or a $C_{1-6}$alkyl, $C_{3-7}$cycloalkyl, $C_{3-6}$alkenyl, phenyl or phenyl $C_{1-3}$alkyl group, and each of the other two groups, which may be the same or different, represents a hydrogen atom or a $C_{1-6}$ alkyl group;

n represents 1, 2 or B 3;

Q represents a hydrogen atom, a halogen atom or a hydroxy, $C_{1-4}$alkoxy, phenyl $C_{1-3}$alkoxy or $C_{1-6}$alkyl group, or a group $-NR^4R^5$ or $-CONR^4R^5$, (wherein $R^4$ and $R^5$, which may be the same or different, each represents a hydrogen atom or a $C_{1-4}$alkyl or $C_{3-4}$alkenyl group, or together with the nitrogen atom to which they are attached form a saturated 5 to 7 membered ring); and X represents an oxygen or a sulphur atom; or a physiologically acceptable salt or solvate thereof.

2. A compound according to claim 1 in which $R^1$, $R^2$ and $R^3$ each independently represent a hydrogen atom or a $C_{1-6}$alkyl group.

3. A compound according to claim 1 in which Im represents an imidazolyl group of formula (a) or (b).

4. A compound according to claim 3 in which $R^1$ and $R^2$ each represents a hydrogen atom and $R^3$ represents a $C_{1-6}$alkyl group.

5. A compound according to claim 1 in which Im represents an imidazolyl group of formula (c), $R^1$ represents a $C_{1-3}$alkyl group and $R^2$ and $R^3$ each represent a hydrogen atom.

6. A compound according to claim 1 in which $R^1$, $R^2$ and $R^3$ each represent a hydrogen atom or a $C_{1-3}$alkyl group, and Q represents a hydrogen atom.

7. A compound according to claim 6 in which n represents 2, and Im represents an imidazolyl group of formula (a) or (b).

8. A compound selected from:

3,4-dihydro-2-[(5-methyl-1H-imidazol-4-yl)methyl]-1(2H)-dibenzofuranone;

3,4-dihydro-2-[(5-methyl-1H-imidazol-4-yl)methyl]-1(2H)-dibenzothiophenone;

and physiologically acceptable salts and solvates thereof.

9. A pharmaceutical composition for treating a condition mediated through 5-$HT_3$ receptors which comprises an effective amount to relieve said condition of at least one compound of general formula (I) as defined in claim 1 or a physiologically acceptable salt or solvate thereof together with at least one physiologically acceptable carrier or excipient.

10. A method of treating a condition mediated through 5-$HT_3$ receptors which comprises administering to a patient an effective amount of a compound of formula (I) as defined in claim 1 or a physiologically acceptable salt or solvate thereof to relieve said condition.

* * * * *